US00PP08210P

United States Patent [19]

VandenBerg

[11] Patent Number: Plant 8,210

[45] Date of Patent: Apr. 20, 1993

[54] CHRYSANTHEMUM PLANT NAMED LEXUS

[75] Inventor: Cornelis P. VandenBerg, Salinas, Calif.

[73] Assignee: Yoder Brothers, Inc., Barberton, Ohio

[21] Appl. No.: 756,840

[22] Filed: Sep. 9, 1991

[51] Int. Cl.[5] ..... A01H 5/00

[52] U.S. Cl. ..... Plt./82.2

[58] Field of Search ..... Plt./82.2

*Primary Examiner*—Howard J. Locker

*Attorney, Agent, or Firm*—Foley & Lardner

[57] ABSTRACT

A Chrysanthemum plant named Lexus particularly characterized by its flat capitulum form; daisy capitulum type; yellow ray floret color; diameter across face of capitulum of 76 to 89 mm when fully opened, when grown as a single stem spray cut mum; flowering response under normal temperatures is 50 to 54 days after start of short days; plant height is 91 to 102 cm when grown with 6 to 8 long days prior to start of short days; peduncle length of the first lateral at flowering after removing the apical bud without growth regulator applications is 8 to 13 cm; peduncle length of the fourth lateral at flowering is 13 to 18 cm; and terminal spray formation.

3 Drawing Sheets

The present invention comprises a new and distinct cultivar of Chrysanthemum, botanically known as *Dendranthema grandiflora,* and referred to by the cultivar name Lexus.

Lexus, identified as 1847 (85-284003), was originated from a cross made by Cornelis P. VandenBerg in a controlled breeding program in Salinas, Calif., in 1985.

The female parent of Lexus was an unnamed seedling identified as 0669 (79-T59001) and described as a cut spray mum with a flat capitulum form; a daisy capitulum type; a white ray floret color; a diameter of capitulum of 89 to 95 mm when fully open; flowering response to short days of 52 to 54 days; a plant height of 91 to 109 cm when grown with 14 long days prior to start of short days; a peduncle length of the first lateral of 3 to 13 cm and of the fourth lateral of 8 to 23 cm; and a terminal spray formation. The above characteristics are based on plants grown in Salinas, Calif. The female parent was discarded from all programs in February, 1986.

The male parent of Lexus was an unnamed seedling identified as 5846 (82-J14015) and described as a cut spray mum with a flat capitulum form; a daisy capitulum type; an ivory-white ray floret color; diameter of capitulum of 64 to 76 mm; a flowering response of 60 to 62 days; a plant height ranging from 102 to 117 cm when grown with 12 to 14 long days prior to start of short days; a peduncle length of the first lateral of 10 to 15 cm and of the fourth lateral of 10 to 20 cm; and a terminal spray formation. The above characteristics are based on plants grown in Salinas, Calif. The male parent was discarded from all programs in May, 1986.

Lexus was discovered and selected as one flowering plant within the progeny of the stated cross by Cornelis P. VandenBerg in April, 1986, in a controlled environment in Salinas, Calif.

The first act of asexual reproduction of Lexus was accomplished when vegetative cuttings were taken from the initial selection in June, 1986, in a controlled environment in Salinas, Calif., by technicians working under supervision of Cornelis P. VandenBerg.

Horticultural examination of controlled flowerings of successive plantings has shown that the unique combination of characteristics as herein disclosed for Lexus are firmly fixed and are retained through successive generations of asexual reproduction.

Lexus has not been observed under all possible environmental conditions. The phenotype may vary with variations in environment such as temperature, light intensity and daylength, without, however, any variance in the genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Lexus, which, in combination, distinguish this Chrysanthemum as a new and distinct cultivar:

1. Flat capitulum form.
2. Daisy capitulum type.
3. Yellow ray floret color.
4. Diameter across face of capitulum of 76 to 89 mm when fully opened, when grown as a single stem spray cut mum.
5. Flowering response under normal temperatures is 50 to 54 days after start of short days.
6. Plant height is 91 to 102 cm when grown with 6 to 8 long days prior to start of short days.
7. Peduncle length of the first lateral at flowering after removing the apical bud without growth regulator applications is 8 to 13 cm; peduncle length of the fourth lateral at flowering is 13 to 18 cm.
8. Terminal spray formation.

The accompanying photographic drawings show typical inflorescence and leaf characteristics of Lexus, with the colors being as nearly true as possible with illustrations of this type.

Sheet 1 is a color photograph of Lexus grown as a single stem spray cut mum.

Sheet 2 is a black and white photograph of three views of the inflorescence of Lexus.

Sheet 3 is a black and white photograph showing the upper and under sides of the leaves of Lexus at 3 stages of development (mature, intermediate and immature).

In sheets 2 and 3 a measuring tape in centimeters has been added.

Of the commercial cultivars known to the inventor, the most similar in comparison to Lexus is the cultivar identified as Mellow, disclosed in U.S. Plant Pat. No. 5,166. Reference is made to attached Chart A, which compares certain characteristics of Lexus to the same characteristics of Mellow.

Similar traits are capitulum form and type, and spray formation. The ray floret color of both cultivars is described as yellow, but Lexus has a darker, deeper yellow ray floret color than Mellow. Lexus has a smaller diameter capitulum, an earlier flowering response to short days, a shorter plant height, and longer peduncles when compared with Mellow.

In the following description color references are made to The Royal Horticultural Society Colour Chart. The color values were determined on plant material grown as a single stem spray cut mum in Salinas, Calif., on Jan. 22, 1990.

Classification:

*Botanical.*—*Dendranthema grandiflora* cv. Lexus.

*Commercial.*—Daisy spray cut mum.

INFLORESCENCE

A. Capitulum:

*Form.*—Flat.

*Type.*—Daisy.

*Diameter across face.*—76 to 89 mm when fully opened.

B. Corolla of ray florets:

*Color (general tonality from a distance of three meters).*—Yellow.

*Color (upper surface).*—9A to 9B.

*Color (under surface).*—9C.

*Shape.*—Straight, oblong. Immature ray florets are convex.

C. Corolla of disc florets:

*Color (mature).*—14A.

*Color (immature).*—144A to 144B.

D. Reproductive organs:

*Androecium.*—Present on disc florets only; moderate pollen.

*Gynoecium.*—Present on both ray and disc florets.

PLANT

A. General appearance:

*Height.*—91 to 102 cm when grown in Salinas with 6 to 8 long days prior to start of short days.

B. Foliage:

*Color (upper surface).*—147A.

*Color (under surface).*—147B.

*Shape.*—See photograph.

CHART A

COMPARISON OF LEXUS AND MELLOW

| CHARACTERISTIC | LEXUS | MELLOW |
|---|---|---|
| Ray floret color | Yellow | Yellow |
| Capitulum form and type | Flat daisy | Flat daisy |
| Diameter across face of capitulum | 76 to 89 mm | 89 to 102 mm |
| Flowering response | 50 to 54 days | 54 to 59 days |
| Plant height: | | |
| 6–8 long days | 91 to 102 cm | 104 to 114 cm |
| Peduncle length: | | |
| First lateral | 8 to 13 cm | 15 to 18 cm |
| Fourth lateral | 13 to 18 cm | 23 to 25 cm |
| Spray formation | Terminal | Terminal |

COMPARISONS MADE OF PLANTS GROWN AS SINGLE STEM SPRAY CUT MUMS IN SALINAS, CALIFORNIA

I claim:

1. A new and distinct Chrysanthemum plant named Lexus, as described and illustrated.

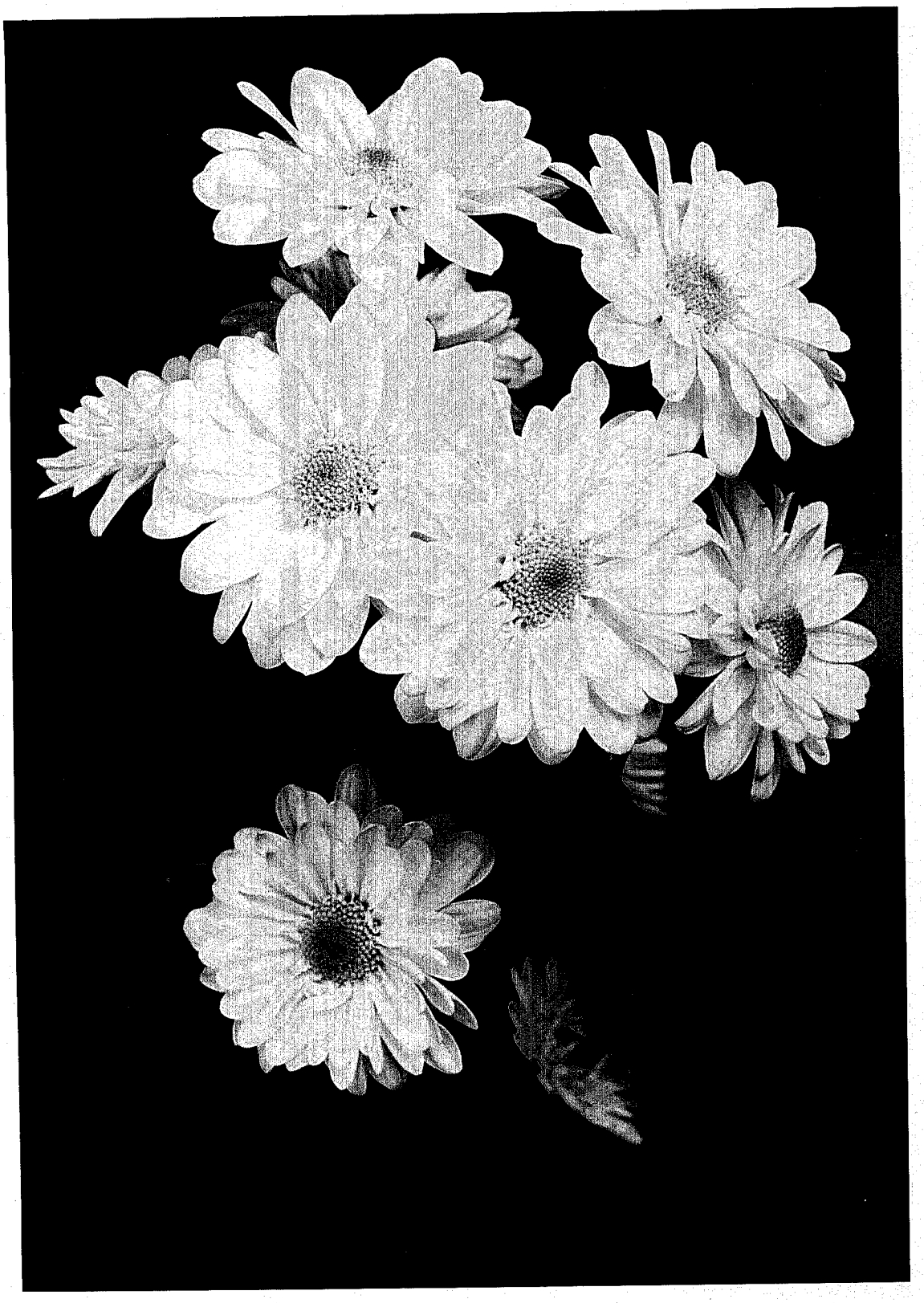

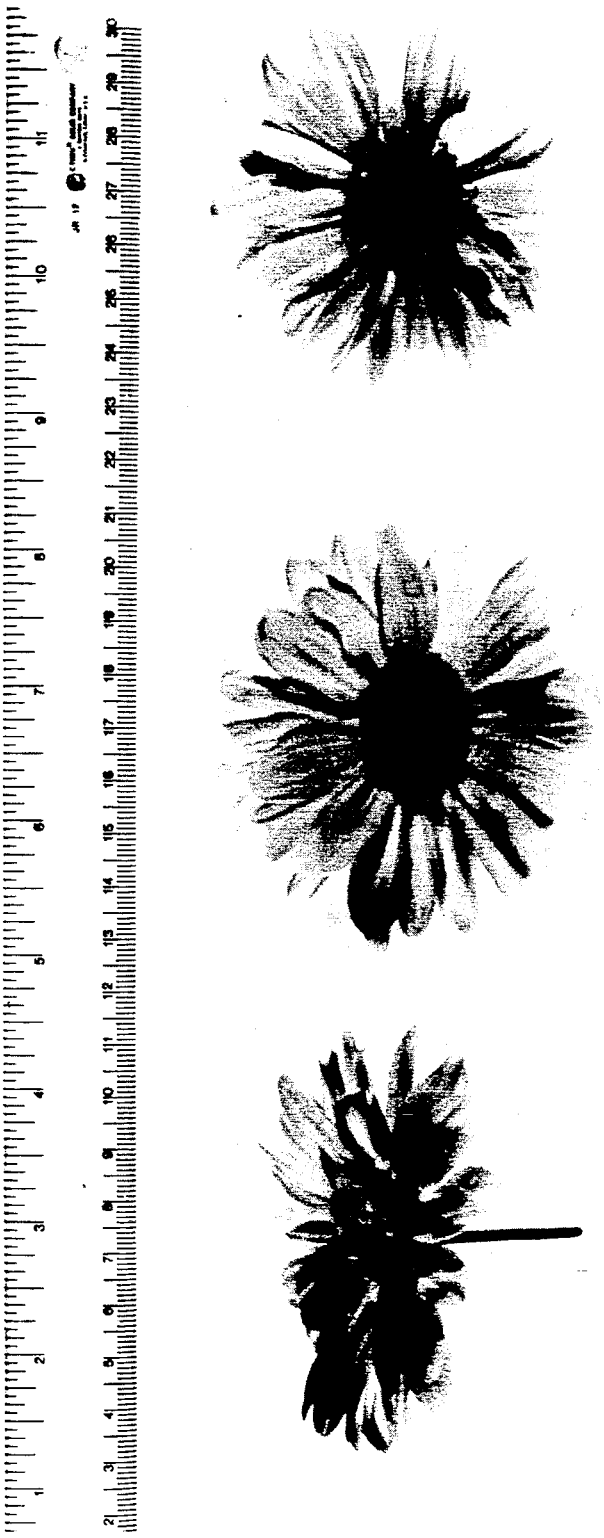

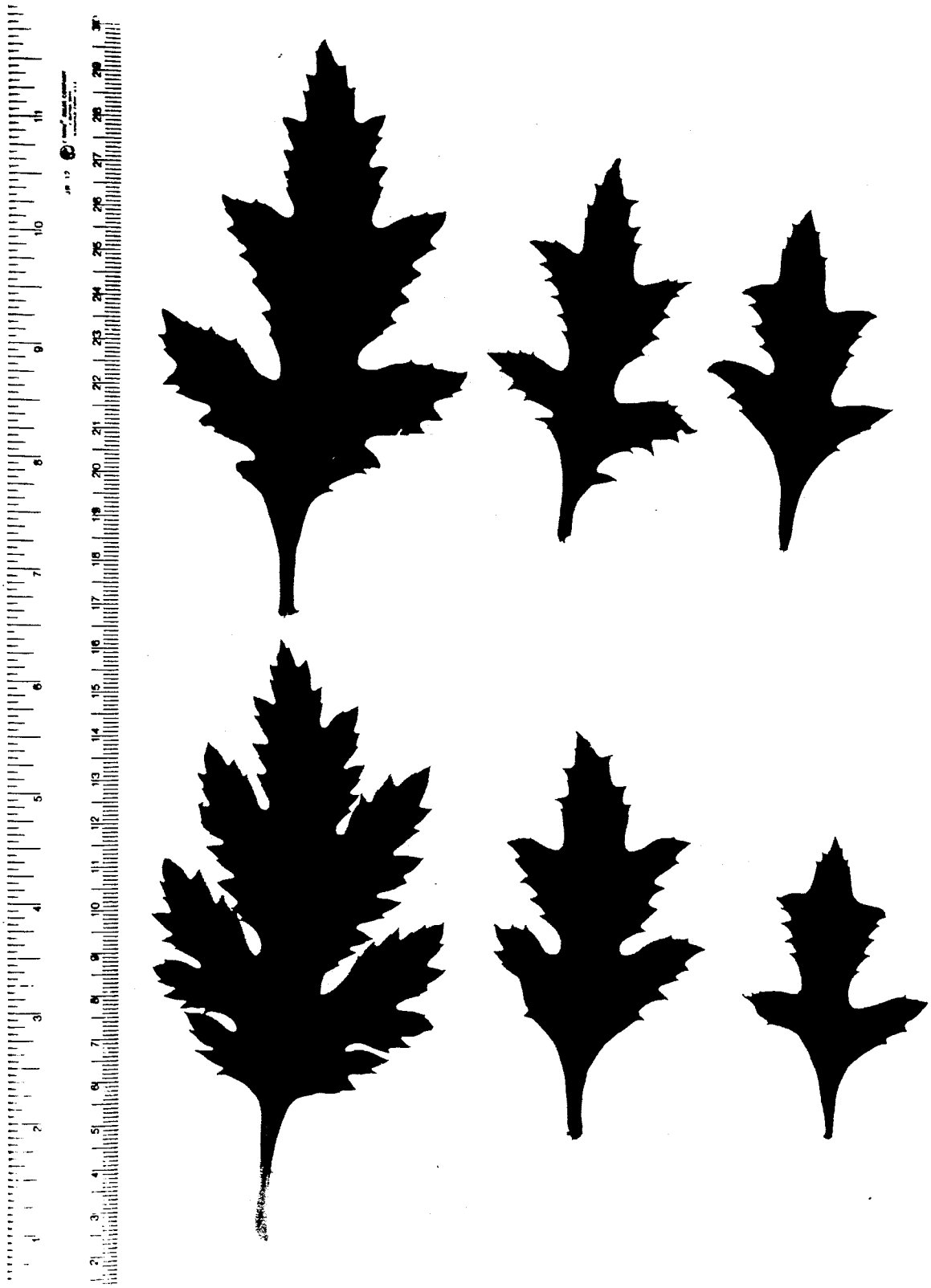

* * * * *